United States Patent [19]

Mauvernay et al.

[11] 4,086,216
[45] Apr. 25, 1978

[54] GLYCOPROTEIN EXTRACTED FROM THE MUSHROOM PSALLIOTA XANTHODERMA AND ITS APPLICATION IN ANTI-VIRAL THERAPY

[75] Inventors: Roland-Yves Mauvernay, Riom; Henri-Jean Pourrat; Jean-Louis Lamaison, both of Clermont-Ferrand, all of France

[73] Assignee: Centre Europeen de Recherches Mauvernay "C.E.R.M.", Riom, France

[21] Appl. No.: 636,941

[22] Filed: Dec. 2, 1975

[30] Foreign Application Priority Data

Dec. 2, 1974  France ............................. 74 39329

[51] Int. Cl.$^2$ ............................................. C07G 7/00
[52] U.S. Cl. ............................. 260/112 R; 424/177; 424/195; 424/85
[58] Field of Search .................. 260/112 R; 424/177, 424/85

[56] References Cited

PUBLICATIONS

Australian J. Exptl. Biol. Med. Sci. 1950, 28, 361–366, Pope.
Australian J. Exp. Biol. 24, 169–173, 1946, Atkinson.
Nature, 174, p. 598 (1954), Atkinson.
The Proteins, vol. III, 1965, pp. 27–30, 78, 80, Neurath.

*Primary Examiner*—Howard E. Schain
*Attorney, Agent, or Firm*—Haseltine, Lake & Waters

[57] ABSTRACT

A process for obtaining an anti-viral substance, useful in herpetiform diseases, from Psalliota Xanthoderma is described.

2 Claims, No Drawings

GLYCOPROTEIN EXTRACTED FROM THE MUSHROOM PSALLIOTA XANTHODERMA AND ITS APPLICATION IN ANTI-VIRAL THERAPY

This invention relates to a new glycoprotein extracted from the carpophores of a mushroom of the order basidiomycetes, Psalliota Xanthoderma, and to its application in the treatment of viral diseases.

The invention also concerns the process which allows high yield isolation of the said glycoprotein, to a high standard of purety, from the fresh mushroom.

After the discovery of penecillin from a fungus of the order ascomycetes, active research of this order and more particularly of the genus streptomyces, led to the discovery of the most important antibiotics (streptomycin, chloromycetin, aureomycin, terramycin, etc.).

This systematic search for antibiotics, led to large scale screening of aqueous extracts from fungi of the order basidiomycetes. These screenings showed very low indices of bacteriostatic activity, although by present day standards this activity cannot be considered significant. This was the case with the work carried out in Great-Britain by W. H. WILKINS [Ann App. Biol, 33, 188 (1946)] on 1000 species, or that of ATKINSON - N. [Austral - J. Exp. Biol. 24 page 169 (1946)] on 200 species, including Balliota Xanthoderma.

In a very small number of cases, the studies led to the isolation of an active principle showing bacteriostatic activity which is still recognized today.

The work of Willstaedt M. and Zetterberg B (Svensk - Kemisk - Tid. 1966, 58, 306) on Lactarius deliciosus can be cited as an example. This allowed the isolation of Lactaroviolin. The work of Lofgren et al (Svensk - Farm - Tidsk. 1949, 53, 321) on Clitocybe nebularis led to the isolation of Nebularine. These two compounds are active on tubercular bacilli.

In contrast, antiviral properties have only been reported on three species of basidiomycetes and in one macromycetes ascomycete. The basidiomycetes are: Calvatia gigantea, the aqueous extract of which is active on various ECHO viruses, Cortinellus shiitake, the aqueous and phenolic extracts of which are active on type A influenza virus, and Amanita phalloides of which the active principle, alpha-amanitine, is active on various RNA viruses, but is strongly toxic to the host cells. The ascomycete is Cordiceps militaris, of which the active principle, Cordicepine, is active on leucovirus. To the best of our knowledge, no research has been carried out up to now on the anti-viral activity of a compound extracted from Psalliota Xanthoderma. The only known works on this mushroom are Australian toxicity studies comparing an aqueous extract of this mushroom with potassium chloride (Pope K. G. Australian.J. Exptl. Biol. Med. Sci. 1950, 28, 361–6).

This invention in contrast, is based on the discovery of certain antiviral properties of a substance obtained from Psalliota Xanthoderma, by a particular extraction process.

The invention relates in the first place to a process which allows the extraction from the carpophore of this mushroom of a substance identified as a glycoprotein. This substance is remarkable in that it shows very low toxicity and high antiviral activity, in particular against Sindbis virus, Herpes virus and vaccinia virus. It shows no bacteriostatic activity.

It relates secondly to the substance obtained by this process and notably defined by this process.

Finally it relates to the applications for this substance in human therapy, in the treatment of herpes like diseases.

The process, according to the invention, basically consists of three successive stages: aqueous extraction, dialysis and lyophilisation, carried out under specific conditions.

In the extraction phase, the carpophores of fresh mushrooms are first lyophilised and then ground and sieved to obtain a semi-fine powder. This powder is placed in an extractor containing 10–40 parts water, maintained at a temperature of 35°–40° C, under stirring.

The extraction is continued for about 30 minutes and then, the vegetable debris is removed by centrifugation. The supernatant is filtered once and then a second time on a finer filter in the presence of a filtration adjuvant eg. diatom powder.

At the end of this first stage, a limpid filtrate is obtained, which in particular contains the substance described in this invention.

In the following stage, the filtrate is first adjusted to pH 6, 5 – 7 and then dialysed at a temperature of between 10° and 15° C.

In the final stage, this previously obtained solution is quick-frozen at - 60° C and then lyophilised for 60–72 hours. The dry product, which represents 4% by weight of the powder used in stage 1, is taken up in 50 times its weight of deionised water and filtered on paper or cellulose or asbestos discs. The solution is then lyophilised for a second time under similar conditions.

The product obtained represents 2% by weight of the powder used in stage 1. It is a brownish powder which gives an extremely well dispersed pseudo-solution which does not flocculate.

The following example gives a detailed description of one method of obtaining the invention. It does not however limit its production to this one described method. 250 g of semi-fine powder (sieve 24/28) of lyophilised Psalliota xanthoderma carpophores, (representing approximately 15% of the weight of the fresh carpophores), are extracted by 5 liters of water at a temperature of 37°–38° C.

The extraction is continued for about 30 minutes, stirring at 150 r.p.m.

Vegetable tissues are removed by centrifugation followed by filtration.

The more dense fractions are removed by 10 minutes centrifugation at 2000 r.p.m. The low density particles in the supernatant are removed by filtration on 0 gauge sintered glass.

50 g. of diatom powder is added to this solution.

A second filtration is carried out under similar conditions, using a finer membrane, eg. No. 1 sintered glass. The cake formed by the filtration adjuvant and the impurities is resuspended in an equal volume of water, and re-filtered on no. 1 sintered glass. This filtrate is added to the previous one.

The limpid solution thus obtained is adjusted to pH 7 and then placed in dialysis tubes. A constant flow of water is maintained into the dialysis tank and the process is allowed to continue for 65 hours at about 10° C.

The potassium chloride concentration, which was 65.5 mg/g before dialysis falls fo 2 mg/g. The latter figure is considered as showing quantitative elimination of potassium chloride during the dialysis.

The dialysed solution is then rapidly frozen at about −60° C and lyophilised fairly slowly so that the operation takes about 65 hours.

The yield is 10–2 g of lyophilised powder, representing 4% of the initial weight.

This lyophilisate is taken up in 50 times its weight of cold deionised water. The insoluble part is easily removed by paper filtration. The filtered solution, which has a pH of about 8–4, is adjusted to pH 6–5 by addition of mineral acid.

This solution is frozen and then lyophilised as previously described.

5 g. of brownish powder are obtained with the following physico-chemical characteristics:

Spectral analysis of this powder (hereafter termed PX) in ultraviolet and infra-red light gives the characteristics lines of proteins.

U.V.: absorption maximum at 277–8nm (manometer)
I.R.: peaks at 3300, 2950, 1645, 1540, 1450, 1410 cm$^{-1}$ More precisely, it is a glycoprotein consisting of 40% proteins and 10–12% sugars. The residue is made up of adsorbed resins. Determination of the sugar content was carried out by the sulphuric anthrone method taking glucose as a reference.

The amount of protein was determined by the Folin method, and is expressed as control serum albumin.

The sugars present in this glycoprotein are bound sugars or polysaccharides. They consist mainly of galactose. Mannose, small amounts of glucose and traces of rhamnose have also been identified.

The determination of the amino acids present in the protein fraction of this glycoprotein, were performed using a Technicon auto-analyser.

The following results are expressed as amino acid residues per 1000 residues.

ASP 135-28, THR 64-41, SER 80-75, GLU 118-35, PRO 46-37, GLY 114-62,
ALA 80-69, GYS/2 16-95, VAL 60-96, MET 13-31, ILEU 42-82, LEU 62-05,
TYR 29-37, PHE 35-07- LYS 44-73, HIS 17-74, ARG 36-55.

These characteristics were found to be similar within the limits of experimental error, for different batches, independant of the time or place of collection of the Psalliota xanthoderma.

The compound PX was tested with respect to various viruses, and the most interesting results are given below. These concern Sindbis virus, other DNA or RNA viruses, Herpes virus and Vaccinia virus.

The study with Sindbis virus, was carried out using the concentration gradient method. In this method, a suspension of Sindbis virus (producing about 100 plaques per dish) is placed on a monocellular layer of chick embryo fibroplast in a Petri dish. After 1 hour adsorption, a first layer of gel medium is added, inclining the dish so that a thickness varying between 0 and 5 mn is obtained. After this layer has set, a second identical layer containing however the PX test compound is added.

During the incubation, which continues for 48 hours at 37° C, and at equilibrium, it can be seen that the concentration increases regularly, following the axe of the initial inclination, from 0 to the maximal concentration assayed.

At the end of the experiment, the toxicity of the product on the cells is first noted. This is shown by alkalinisation of the medium. It is a rough, macroscopic evaluation of toxicity which shows a cellular death.

The complete absence of plaques without cellular destruction situates the zone of activity. A decrease in plaque size indicates poor diffusion of the virus and therefore a certain inhibitory effect.

The following diagrams show the results obtained for three different doses, both with amantadine hydrochloride and the compound PX.

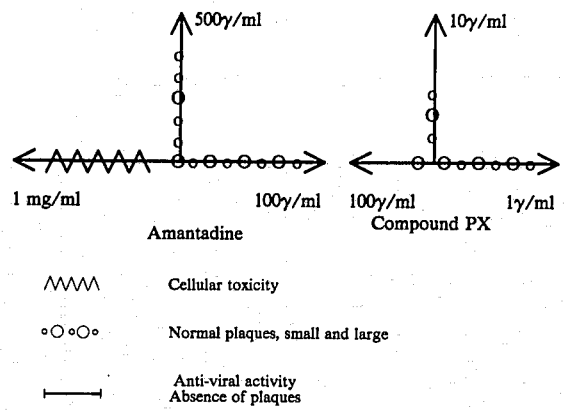

It can be seen that the activity of the compound PX is clear up to 5 γ/ml without there being any toxicity for concentrations less than 100 γ/ml For amantadine, the classical reference antiviral, cellular toxicity was seen at 500 γ/ml, i.e. twice the threshold of antiviral activity which was 250 γ/ml.

The activity of compound PX, on Herpes virus, and vaccinia virus was tested in vitro, by showing a possible reduction of the cytopathogenic effect of this virus on KB cells. It was found that compound PX at a concentration of 100 mcg/ml, reduced the cytopathogenic effect of Herpes or Vaccinia virus by 50%.

The action of compound PX on Herpes virus was confirmed "in ovo": The chorioallantoic membrane of 11 day old embryonated eggs was innoculated with compound PX. After 24 hours they were innoculated with Herpes virus. After 72 hours incubation at 37° C, the chorioallantoic membrane was removed and the number of pustules formed counted and compared with control eggs which had not received compound PX. These latter usually show about 50 pustules.

For 50 mcg of compound PX per egg, the number of pustules was reduced to 3; for 25 mcg, it was reduced to 6.

This antiviral activity is also remarkable in that it is a true antiviral activity. Complementary studies have in fact shown that compound PX is not an Interferon inducer.

Possible bacteriostatic properties have been studied in relation to three strains of micro-organisms:

Staphylococcus Aureus Oxford, Escherichia coli 1P, 548, and Candida Albicans I.P. The study was carried out by the method of dilution in liquid medium (Trypticase soja broth for Staphylococcus and Colibacillus, and Sabouraud liquid medium for Candida). The innocula were taken from a 24 hour culture, final dilutions being $10^{-3}$ for Staphylococcus, $5 \times 10^{-4}$ for Colibacillus and $10^{-4}$ for Candida.

The minimum inhibitory concentrations for compound PX, after 24 hours at 37° (Staphylococcus and Colibacillus) or 30° for Candida, were greater than 5000

μg/ml. It can be concluded therefore that compound PX is not bacteriostatic.

Finally, it should be noted that the remarkable lack of toxicity of compound PX, seen with the gradient concentration method has been confirmed by acute toxicity studies carried out intravenously in mice.

This study was carried out in groups of 18 animals, and the LD 50 calculated by the method giving best linearisation of results.

The calculated LD50 is 318 mg/kg, the confidence limits at 5% being 268-369.

The previous results make it possible to envisage using compound PX in human therapy, in particular for the treatment of Herpes, or any disease with herpetic symptoms.

Compound PX could be administered orally or by general routes, associated with the usual pharmaceutical excipients, in a form compatible with the particular disease. It could be used in the form of a 10 μg/ml eyewash for preparation immediately before use, or in an injectable or oral form at daily doses of between 10 and 300 mg.

We claim:

1. Process for obtaining a substance, possessing anti-viral properties useful in herpetiform diseases from Psalliota Xanthoderma which comprises subjecting the carpophores of Psalliota Xanthoderma to the successive steps of aqueous extraction, dialysis and finally lyophilization wherein
   (a) the aqueous extraction is carried out by the addition of 10-40 parts water to previously lyophilised, ground and sieved fresh mushrooms, followed by mixing of the suspension for about 30 minutes at 35°-50° C and collection of the extraction fluid by filtration;
   (b) the dialysis is carried on the filtrate from the aqueous extraction phase, previously adjusted to pH 6.5 to 7.0, for 60-70 hours at a temperature of about 10°-15° C; and
   (c) the lyophilization is carried out by the freezing, at −60° C, of the dialysed solution followed by slow lyophilization for 60-70 hours.

2. Process as described in claim 1, wherein the lyophilisate obtained is taken up in deionised water and submitted to a second lyophilisation after filtration and acidification to pH 6-5.

* * * * *